(12) United States Patent
Lundin et al.

(10) Patent No.: US 11,547,322 B2
(45) Date of Patent: Jan. 10, 2023

(54) DEVICE AND METHOD FOR NON-INVASIVE ANALYSIS OF PARTICLES DURING MEDICAL VENTILATION

(71) Applicants: Stefan Lundin, Gothenburg (SE); Anna-Carin Olin, Vastra Frolunda (SE)

(72) Inventors: Stefan Lundin, Gothenburg (SE); Anna-Carin Olin, Vastra Frolunda (SE)

( * ) Notice: Subject to any disclaimer, the term of this patent is extended or adjusted under 35 U.S.C. 154(b) by 884 days.

(21) Appl. No.: 14/377,588

(22) PCT Filed: Feb. 8, 2013

(86) PCT No.: PCT/EP2013/052620
§ 371 (c)(1),
(2) Date: Aug. 8, 2014

(87) PCT Pub. No.: WO2013/117747
PCT Pub. Date: Aug. 15, 2013

(65) Prior Publication Data
US 2016/0000358 A1    Jan. 7, 2016

Related U.S. Application Data

(60) Provisional application No. 61/596,444, filed on Feb. 8, 2012.

(30) Foreign Application Priority Data

Feb. 8, 2012    (SE) .................................. 1250093-0

(51) Int. Cl.
A61B 5/00        (2006.01)
A61B 5/08        (2006.01)
A61B 5/097       (2006.01)
A61M 16/00       (2006.01)
G01N 33/497      (2006.01)
(Continued)

(52) U.S. Cl.
CPC ................ *A61B 5/082* (2013.01); *A61B 5/08* (2013.01); *A61B 5/097* (2013.01); *A61B 5/4836* (2013.01);
(Continued)

(58) Field of Classification Search
CPC .................................................... A61B 5/0836
See application file for complete search history.

(56) References Cited

U.S. PATENT DOCUMENTS

2007/0157931 A1    7/2007  Parker
2008/0202521 A1*   8/2008  Mitton .............. A61M 16/0051
                                                              128/204.21
(Continued)

FOREIGN PATENT DOCUMENTS

WO    WO 2006/076265    7/2006
WO    WO2009/045163     4/2009

OTHER PUBLICATIONS

WO2013/117747 Publication and International Search Report dated Aug. 15, 2013 (1 pages).
(Continued)

*Primary Examiner* — Etsub D Berhanu
(74) *Attorney, Agent, or Firm* — Knobbe Martens Olson and Bear, LLP

(57) ABSTRACT

A diagnostic device is disclosed for characterisation of particles from a patient's airways, such as a lung, when ventilated by a ventilator, and/or for control thereof, comprising a particle detecting unit configured to be connected to a conduit for passing expiration fluid from said patient, for obtaining data related to particles being exhaled from said patient's airways.

16 Claims, 8 Drawing Sheets

(51) Int. Cl.
  *G01N 15/10* (2006.01)
  *A61M 16/08* (2006.01)
  *A61M 16/10* (2006.01)
  *G01N 15/02* (2006.01)
  *G01N 1/22* (2006.01)
  *G01N 15/00* (2006.01)

(52) U.S. Cl.
  CPC .... *A61M 16/0003* (2014.02); *A61M 16/0069* (2014.02); *A61M 16/085* (2014.02); *A61M 16/0833* (2014.02); *A61M 16/0875* (2013.01); *A61M 16/104* (2013.01); *A61M 16/105* (2013.01); *G01N 15/10* (2013.01); *G01N 33/497* (2013.01); *A61M 2202/0241* (2013.01); *A61M 2205/3334* (2013.01); *G01N 15/02* (2013.01); *G01N 2001/2244* (2013.01); *G01N 2015/0026* (2013.01); *G01N 2015/0261* (2013.01)

(56) References Cited

U.S. PATENT DOCUMENTS

| | | | |
|---|---|---|---|
| 2008/0243007 A1* | 10/2008 | Liao | A61B 5/0215 600/486 |
| 2008/0262370 A1* | 10/2008 | Varney | A61B 5/0836 600/532 |
| 2010/0245097 A1 | 9/2010 | Sung | |
| 2010/0297635 A1* | 11/2010 | Olin | A61B 5/411 435/6.11 |
| 2011/0082380 A1* | 4/2011 | Breen | A61M 16/12 600/532 |

OTHER PUBLICATIONS

EPO Communication for EP Application No. 13 703 805.5-1115 dated Jan. 17, 2020; 5 pages.

* cited by examiner

DEVICE AND METHOD FOR NON-INVASIVE ANALYSIS OF PARTICLES DURING MEDICAL VENTILATION

BACKGROUND OF THE DISCLOSURE

Field of the Invention

This invention pertains in general to the field of breathing apparatuses, such as medical ventilators or anaesthesia machines. More particularly the invention relates to continuously diagnosing and monitoring of patients during ventilation or respiration.

Description of the Prior Art

It is known that mechanical ventilation provided by ventilators may induce lung injuries. This is in particular related to application of non physiological excess pressures when mechanically ventilating the lungs. For example structural damages such as over-distension of the lungs, such as alveoli rupture, as well as abrasive damages to the lungs due to phasic opening or closing may occur.

Mechanical ventilation lowers the levels of surfactant in the lungs with a higher risk of collapsing of the distal airways and alveolar. This will cause increased levels of released inflammatory markers, i.e. cytokines. Inflammatory markers may be established through bronchoalveolar lavage (BAL) where e.g. 50-100 ml isotonic saline is instilled into the lung, recollected and analysed for bio-markers and surfactants.

It has been shown that "protective" strategies with lower tidal volumes and higher end expiratory-pressure may be advantageous to lower pulmonary cytokines and systematic release of cytokines, measured using BAL. There are evidences suggesting that a spill-over of mediators to the cardiovascular system may help to cause organ dysfunction or failure, such as renal insufficiency.

For critically ill patients with a high demand of oxygen, BAL is an invasive method that worsens the oxygenation and is restrictively used, for example, for infection diagnostic at stable patients.

US 2007/0157931 relates to a disclosure of systems, methods, and devices for controlling delivery of aerosolized formulations to patients in need of treatment, which optimizes aerosol deposition to the respiratory tract of the patient and can be adapted for use in spontaneously breathing patients or in those requiring mechanical ventilation.

The disclosure in this document does not teach that particles origin from the airways may be used for diagnosis or monitoring of a condition of the airways, such as parts of the lungs, of a patient.

Neither does it disclose that these characterizations of these particles may be used for optimization of, for example, PEEP. The only disclosure is related to determining a delivered dose of aerosolized formulation to a patient by monitoring exhaled waste and having knowledge of respiratory parameters, for example, the tidal volume.

Thus, there is a need for an improved method, device and/or system for non-invasive, online diagnosis and/or monitoring of a ventilated patient's airway (e.g. lung) condition. Such a method, device and system can provide information to facilitate adjustments of the ventilator by a medical doctor. Thereby, the possibilities of a more careful ventilation treatment may increase and in the end a higher likelihood of survival of critically ill patients.

Further, it would be advantageous if the method, device and/or system could be used to control and optimise the mechanical ventilator's parameters, such as providing feedback to the ventilator based on information provided from diagnosis and/or monitoring of a ventilated patient's airways. Further advantageous would be improved cost-effectiveness compared to the invasive methods used today.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device, a system, and a method for diagnosing or monitoring a patient ventilated using a mechanical ventilator, according to the appended patent claims.

Examples of the disclosure relate to continuously diagnosing and/or monitoring ventilation or respiration by quantifying, such as by means of counting or weighting, particles in exhaled breath from a patient ventilated by a mechanical ventilator, wherein said particles are formed in the patient's airways, such as originating from the respiratory tract lining fluid (e.g. in the lungs). More particularly the provided information may be used to control the ventilator. In particular breathing patterns or mechanical breathing control modes of the ventilator may be controlled or adjusted based on the provided information.

According to aspects of the disclosure, a diagnostic device is provided for characterization of particles from a patient's airways, such as a lung, when ventilated by a ventilator. In some examples, the device may also be used for controlling of the medical ventilator using the obtained information from the characterization of the particles. The device comprising a particle detecting unit configured to be connected to a conduit for passing expiration fluid from the patient. Further, the particle detecting unit is configured for obtaining data related particles exhaled from the patient's airways.

Additionally, the device may have a control unit configured for analyzing the particle data to diagnose and/or monitor a condition of the patients.

The main particles are aerosols being released from a patient's airways, e.g. part of the respiratory systems, such as a lung. A particle in this context means solid, liquid and/or liquid-coated solid objects, which are often suspended in a gas, normally but not necessarily air. Some of the particles of interest may be endogenous particles. Object sizes normally but not necessarily being larger than 0.005 micrometre and normally, but not necessarily, being smaller than 15 micrometre, such as between 0.1 to 15 micrometre, such as between 0.3 to 10 micrometre, such as between 0.3 to 5 micrometre. By size is meant either aerodynamic diameter or electrical mobility diameter.

In some examples of the disclosure, the control unit may be configured to adjust the apparatus to provide a mechanical ventilation mode based on the particle data related to particles exhaled from the patient's airways.

According to aspects of the disclosure, a diagnostic system is provided for characterization of particles from a patient's airways, such as a lung, when ventilated by a ventilator.

In some examples, the device may also be used for controlling of the medical ventilator using the obtained information from the characterization of the particles. The system comprising, a particle detecting unit configured to be connected to a conduit for passing expiration fluid from the patient. The particle detecting unit is configured for obtaining particle data related to particles exhaled from the patient's airways. The system may further comprise a particle collection unit, such as an impactor, configured to be connected to the conduit downstream said ventilator.

In some examples of the disclosure, the particle collection unit comprises collection plates for collecting the exhaled particles. The collection plates are positioned so that the particles may be sorted according to their size or mass. Hence a particle profile may be obtained.

By analyzing the chemical content of the particles possibilities of detecting diseases or damages to the airways, such as lungs may be provided. The obtained information may be used for diagnosis, monitoring and/or treatment of a patient Alternatively, the particle collection unit may also be a particle trap (adsorptive, cryogenic, chemical), or at least one filter, or a collection chamber, or electrostatic collection components, or sampling bags, or canisters, or Solid-phase extraction (SPE) membrane, or sorbent tubes, or condensation components (such as surface condensation collectors), or utilizing surface functionalization or derivation, or any other type of collectors suitable for collecting or capturing particles from exhaled fluids.

According to another aspect of the disclosure, a method for diagnosing or monitoring a condition of a patient connected to a ventilator is provided. The method comprising, providing a particle detecting unit configured to be connected to a conduit for passing expiration fluid from the patient's airways, and obtaining data related particles being exhaled from the patient's airways.

Further examples of the disclosure provides use of a particle counter to measure a number of particles in exhaled breath from a patient ventilated by a mechanical ventilator or respirator, for diagnosis and/or monitoring of the patient's airways.

Yet another embodiment of the disclosure provides use of a particle counter, wherein data from said particle counter is used for controlling said mechanical ventilator or respirator, such as controlling Positive end Expiratory Pressure (PEEP), or airway pressure, or tidal volume, or continues positive airway pressure (CPAP).

Further examples of the disclosure are defined in the dependent claims, wherein features for the second and subsequent aspects of the disclosure are as for the first aspect mutatis mutandis.

Some examples of the disclosure provide for continuous non-invasive monitoring and/or diagnosis of a patient being ventilated by a mechanical ventilator.

Thus, for example, over-dimension, over-distension, and abrasive damages of the lungs may be avoided.

Some examples of the disclosure also provide for controlling a mechanical ventilator by optimizing the control parameters by using the information provided by the monitoring and/or diagnostic device.

Some examples of the disclosure also provide for a safer and more careful treatment of ventilated critically ill patients, thus increased chance of survival. Further, even patients not suitable to invasive methods, such as BAL, may be diagnosed or monitored without the related drawbacks.

Some examples of the disclosure also provide for a more cost-effective way of monitoring and/or diagnosing patients than normally used methods.

Some examples of the disclosure also provide for a warning of acute respiratory distress syndrome (ARDS), or acute lung injury (ALI), for instance due to trauma; or sepsis; or collapse of lung; or acute lung injury. The warning may be due to detection of a rapid increase in particles in the exhaled breath.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF THE PREFERRED EXAMPLES

Figure 1A:
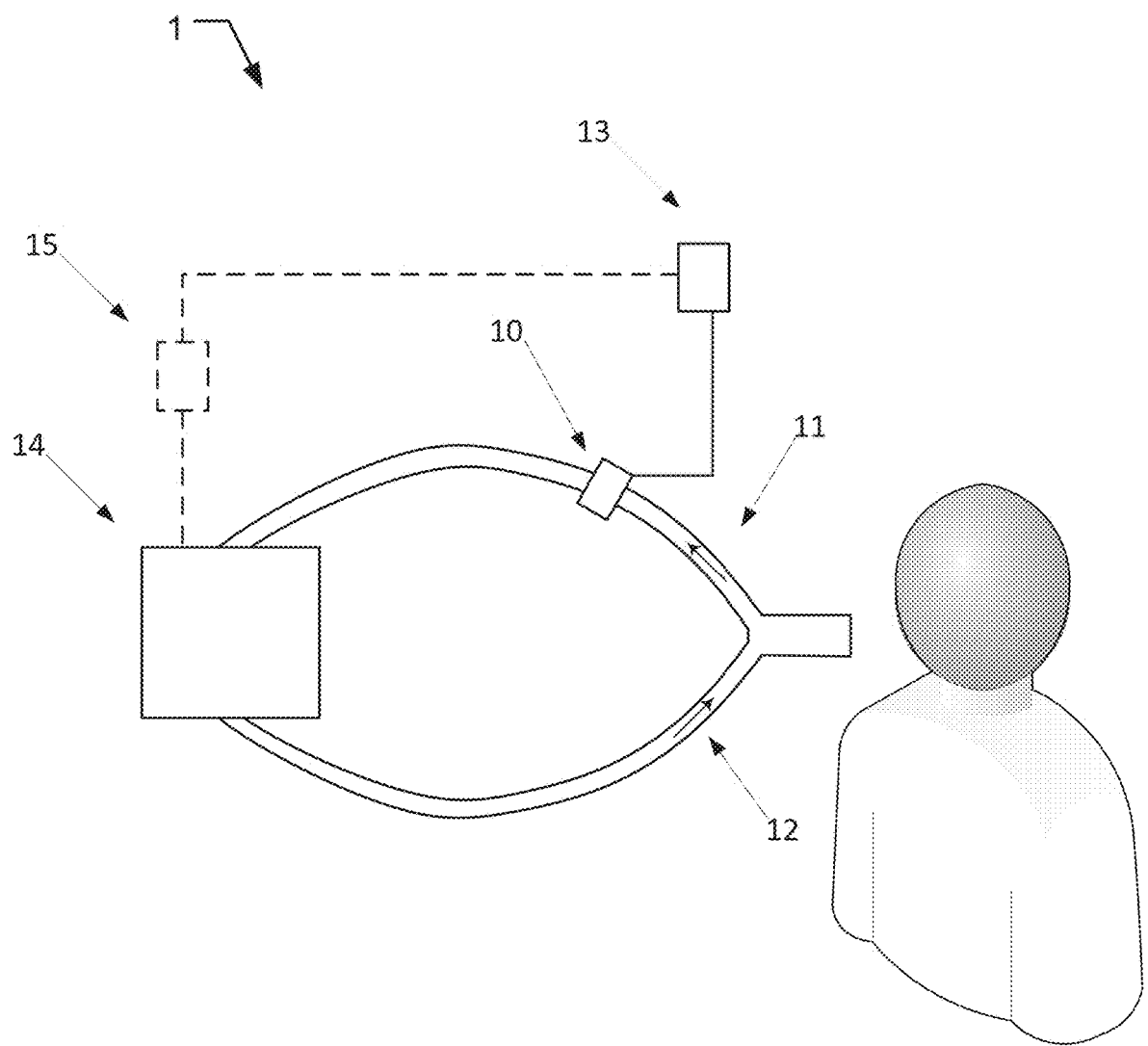
FIG. 1A to FIG. 1E are showing schematic illustrations of different examples of a particle detecting unit connected to a medical ventilator according to the disclosure.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The following description focuses on an embodiment of the present disclosure applicable to a device, system and method for diagnosing and/or monitoring ventilated patients and in particular to quantifying particles in exhaled air from ventilated patients. Additionally, the particles may be sampled or collected for further analyses. Further, the device, system and/or method may be used to control or optimise the parameters of the mechanical ventilator.

When parts of a patient's airways, e.g. the respiratory system, such as the lungs, fail to function correctly, such as a partly collapse of the airways, parts of the airways become narrow and/or alveolar may come into contact. These contacts and/or collapses may result in an increase in particle production during breathing, particularly when these at least partially collapsed parts completely or to some extent phasic open and close.

The present inventors have during their research found out that particles originating from the airways and especially particles generated in the airways of the respiratory system, such as in the lungs, may be used as a marker for the condition of the airways. By continuously quantifying, i.e. counting and/or weighting and/or determining the size of these particles, the condition of a ventilated patient's airways, e.g. lung, may be diagnosed and/or monitored. The amount of quantified particles may indicate the state of the lung. Alternatively and/or additionally information related to an increase or a decrease of detected particles may also be used to provide an indication of the state of a patient's airways.

Further, distributions of particles, such as size distribution characteristics of the particles may also be used for monitoring and/or diagnosis purposes. This applies in particular to particles in the expiratory fluid. In some examples, this may also be applicable to particles in the inspiratory gas. By quantifying the particles in the expiratory airflow, parameters related to the breathing pattern, such as positive end expiratory-pressure (PEEP), or continuous positive pressure (CPAP), may be optimized.

Alternatively and/or additionally, in some examples, a mechanical ventilator can be controlled using feedback from the obtained measurement data and/or signals provided by the particle detecting unit used for quantifying the particles.

Thus collapse of airways or repeated airway closure and opening may be avoided. Further, the information from detecting or quantifying the particles in expiratory gas flow from a patient's airways may give information of the degree of collapse and reopening of portions of a lung.

When applying at least temporary increased PEEP levels to open up part of a patient's airways, such as a lung, the amount of particles in expiratory airflow will decrease with increased PEEP until leveling out, for example, when reaching a plateau. When the plateau has been reached the optimal PEEP may be applied to the airways of the ventilated patient.

When the lung is opened up, the PEEP level or ventilation pressures in general may be lowered again.

This is advantageous as lung damage, for example overdimension, over-distension, from a too high pressure during mechanical ventilation is effectively prevented. A description of examples of suitable ventilation manoeuvres controllable by means of the herein described particle measurement principle is described in an article entitled "Open up the lung and keep the lung open" by B. Lachmann in Intensive Care Med (1992) 18:319-321.

Hence, a PEEP adjustment may be initiated, at least temporarily, based on the particle measurement data. If an at least partly closed lung is detected, a PEEP increase may be initiated, e.g. by a control unit of a ventilator, or software executed in a processing unit thereof, such as the aforementioned control unit. Detection of increasing particle levels is an indication of alveoli recruitment, i.e. opening up the lung.

Additionally and/or alternatively, in some examples, detection of the aforementioned plateau level over a pre-defined time may be taken for aborting a period of increased PEEP.

The inventors have, for example, found out there is a correlation between the proteins in the BAL-liquid and the particles identified in exhaled breath. For instance a PExA-system (such as disclosed in PCT/SE08/51110, incorporated by reference herein in its entirety) may be used for this identification in certain examples. Until now it has been impossible to study this mucus layer and/or respiratory tracked lining fluid non-invasively. Previous studies have mostly used invasive methods, such as BAL.

The particle quantification may be combined with collection of particles for chemical, biological, DNA/RNA/mRNA, virological and bacteriological, or any other analysis of the particles.

The main particles are aerosols, released from a patient's airways, e.g. part of the respiratory systems, such as a lung.

A particle in this context means solid, liquid and/or liquid-coated solid objects, which are often suspended in a gas, normally but not necessarily air. Some of the particles of interest may be endogenous particles. Object sizes normally but not necessarily being larger than 0.005 micrometre and normally but not necessarily being smaller than 15 micrometre. By size is meant either aerodynamic diameter or electrical mobility diameter, suitably aerodynamic diameter.

Various examples will now be elucidated in more detail with reference to the appended FIG. 1A to FIG. 1E. In all illustrations the expiratory airflow is coupled to the mechanical ventilator via suitable patient tubing. Expired gases may further be directed to a collection site, e.g. for contaminated fluids, e.g. via filter systems or to an evacuation system of a central hospital gas evacuation system.

In FIG. 1A, a configuration 1 is illustrated where the particle detecting unit 10 is connected to the expiratory airflow conduit 11 from a patient, here illustrated as connected downstream a Y-piece of the tubing of a mechanical ventilator connectable to a patient (not shown). The inspiratory airflow is connected to the patient through conduit 12. The particle detection unit 10 may be connected to a user interface such as a display or a sound source to provide medical staff, such as doctors or nurses, with patient airway related information.

This information may be used to optimize the parameters of the mechanical ventilator 14.

Alternatively, in some examples of the disclosure, the particle detection unit 10 may be connected to expiratory airflow conduit 11 either inside the ventilator 14 or after the ventilator.

In some examples the particle detection unit 10 and the interface 13 may be connectable to a control unit 15 to automatically control some of the parameters of the mechanical ventilator 14. This may be performed using a feedback loop. Alternatively, or in addition, the obtained related information may be transferred to the ventilator 14 from the detection unit for display on a display unit of the ventilator 14.

The particle detection unit 10 may in some examples be connected directly to the expiratory airflow conduit in a mainstream configuration since it has a low pressure drop impact on the expiratory flow. This is important as expiration is often passive even during mechanical ventilation (maximum gas flow without externally increased obstruction/pressure drop is desired) and/or work of breathing is desired to be kept at a minimum.

The particle detecting unit may quantify the particles, on-line, in the mainstream of the exhaled gas. Additionally the particle detecting unit 10 may in some examples sort the particles according to their mass. Alternatively, and/or additionally, the particles' sizes may also provide a particle distribution profile of the particles. The particle distribution profile is a measure of how many particles of a particular mass or size (or mass or size range) are present in the exhaled air, and can also be used to determine a medical condition of a subject.

The particle detection unit may be, for example, a particle counter such as a Grimm 1.108 optical particle counter (Grimm Aerosol Technik, Ainring, Germany), capable of counting, and sizing particles in 15 size intervals from 0.3 to 20 micrometre. But other optical particle counters such as a Grimm 1.107 and 1.109 may be used. Other manufacturers such as TSI have particle sizers but also time of flight equipment that may be used as particle detection units 10. Other options may be, Non-optical, electrostatically, conductance, condensation particle counters, Quartz Crystal Microbalance (QCM), Surface Plasmon Resonance (SPR) or surface acoustic-wave (SAW) etc.

The particle detecting unit 10 may provide a number size distribution of the measured aerosol or a mass distribution, calculated from the measured number size distribution. In some examples of the particle detecting unit 10, particle-laden gas is passed through a small, well defined, intensely illuminated volume in a manner so that only one particle at a time is illuminated. The illuminated particle gives rise to a pulse of scattered light, the intensity of which is measured. Since the intensity of scattered light depends on the particle size, it is possible to count and size the particles in the air stream. The conduit 11 may comprise a sub-volume where the exhaled gas flow supplies the small well defined volume with a suitably measurable gas flow. By calibration the number of particles passing through the well defined volume is made proportional to the total amount of particles passing through the conduit 11.

Time of flight may also be used as a measurement principle for a particle detecting unit 10. Here, the time of particle propagation from one laser beam to another is measured.

The time it takes for the particle to move from one beam to the other depends on the particle's mass or size which may therefore be measured and characterized.

The particle detecting unit is continuously measuring the number of particles online in the exhaled gas. The sample time to detect a sufficient number of particles before updating the interface 13 of the particle detection unit 10 may be in real time, such as 1 second. It may also be over a time interval such as 2 seconds, such as 4 seconds, such as 10 second. Alternatively the sampling time may be minutes, such as 1 minute, such as 5 minutes, such as 10 minutes such as 30 minutes, such as 60 minutes.

The sampling period may also be defined in exhalations, one exhalation may provide a sufficient number of particles, but particles may also be quantified over repeated exhalations.

Figure 1B:
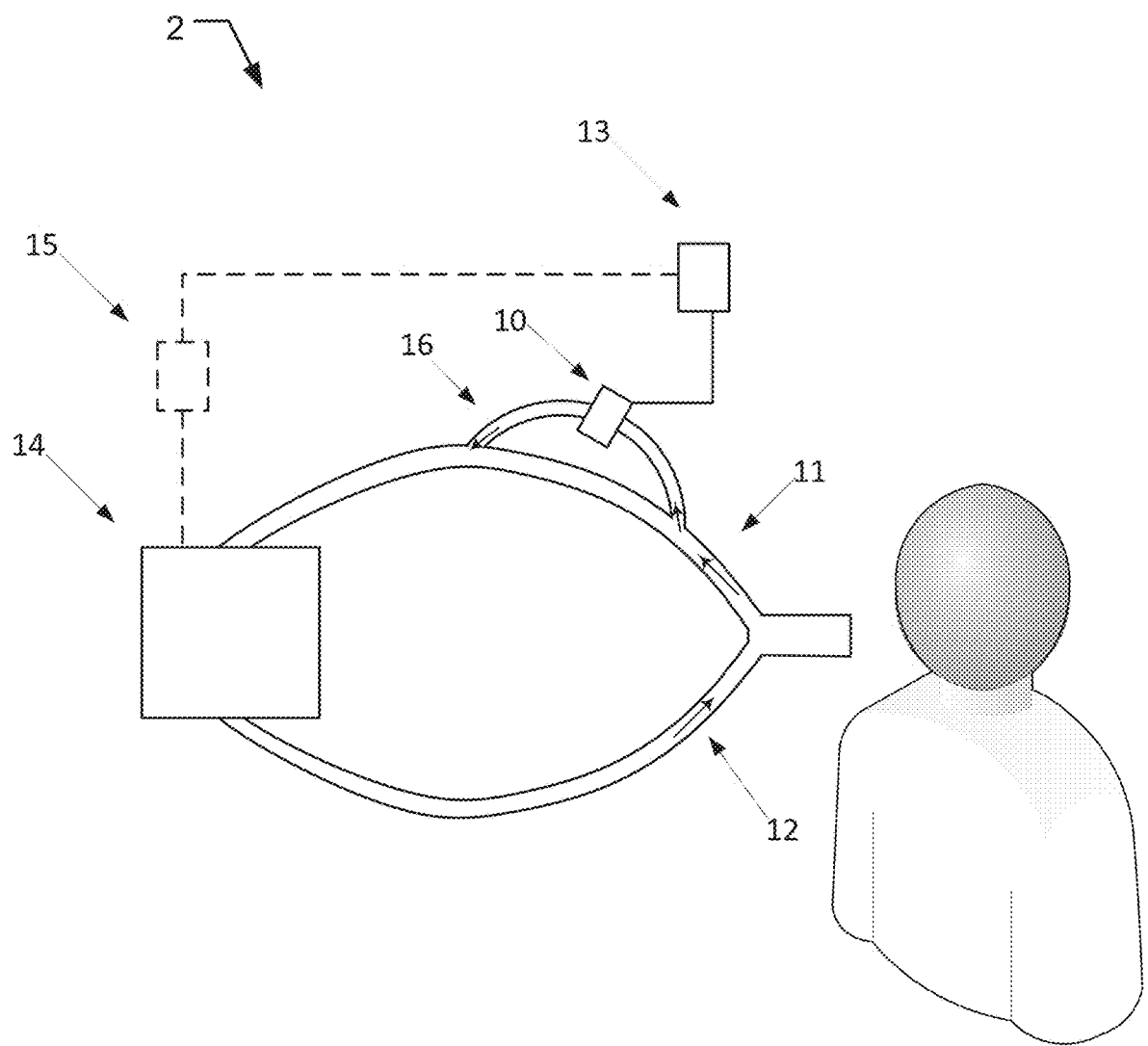

A further configuration 2 of the disclosure is illustrated in FIG. 1B. This example is similar to the configuration illustrated in FIG. 1A. But instead of the particle detecting unit 10 being directly connected to the expiratory conduit 11 it is side-streamed through the conduit 16. This may have the advantage to be easier to connect to the hoses of the ventilator. Moreover, a potential pressure drop in the main lumen 11 is avoided. Further the side stream conduit 16 may have a much smaller diameter making it easier to calibrate than measuring on the larger expiration conduit 11. In the side stream a predefined ratio of the air flow in the conduit 11 is directed and then connected back at a different point. This may be facilitated by a side-stream sampling pump ensuring a constant sampling gas flow. Thus loss of pressure is avoided which may disturb the ventilator 14.

Figure 1C:
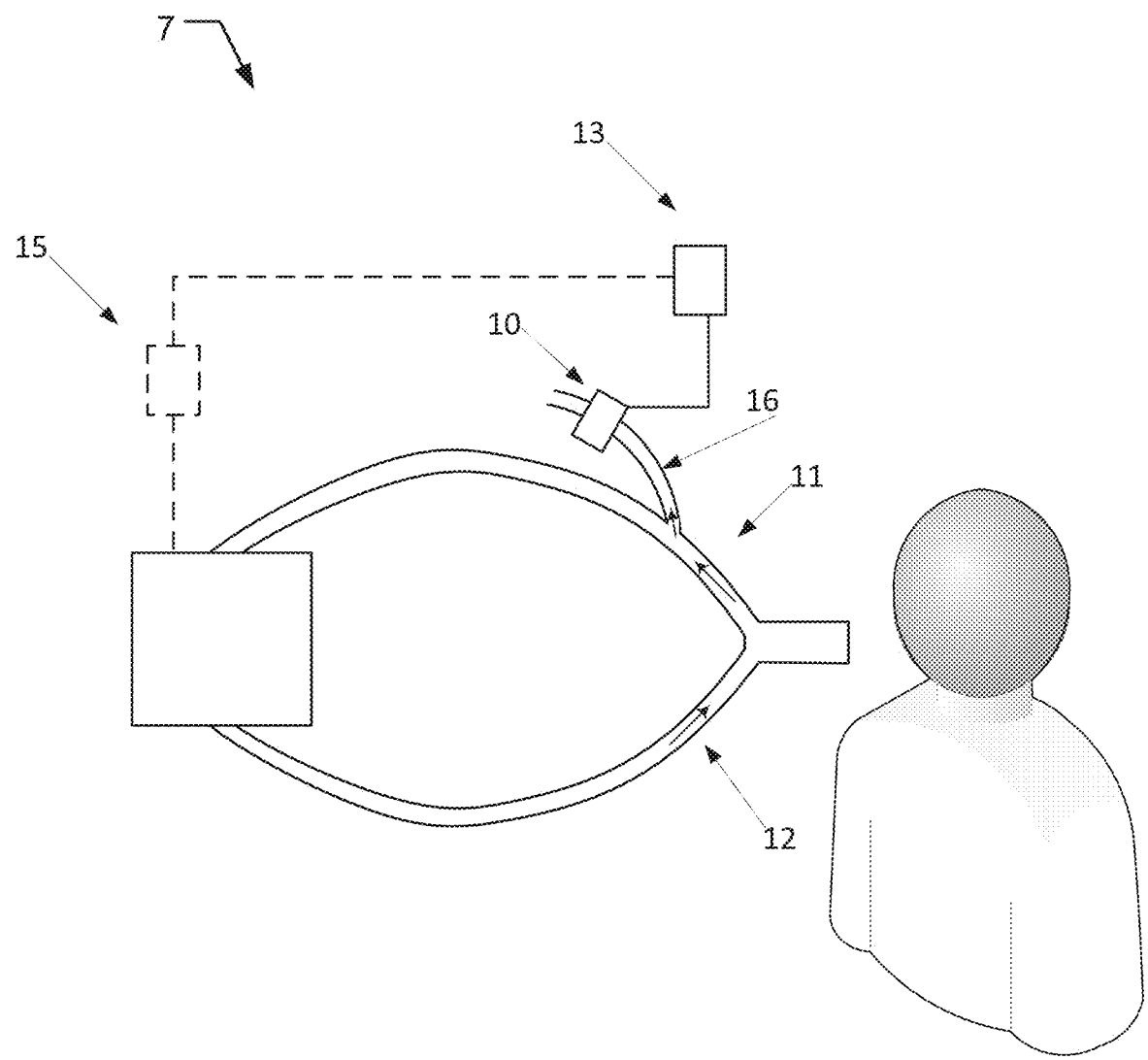

In FIG. 1C an example of an alternative side stream configuration 7 is illustrated. In this example the expired gases is directed into a side stream conduit 16 to be measure using a particle detection unit 10. The expired gases may then be directed to a collection site, e.g. for contaminated fluids, e.g. via filter systems or to an evacuation system of a central hospital gas evacuation system.

Figure 1D:
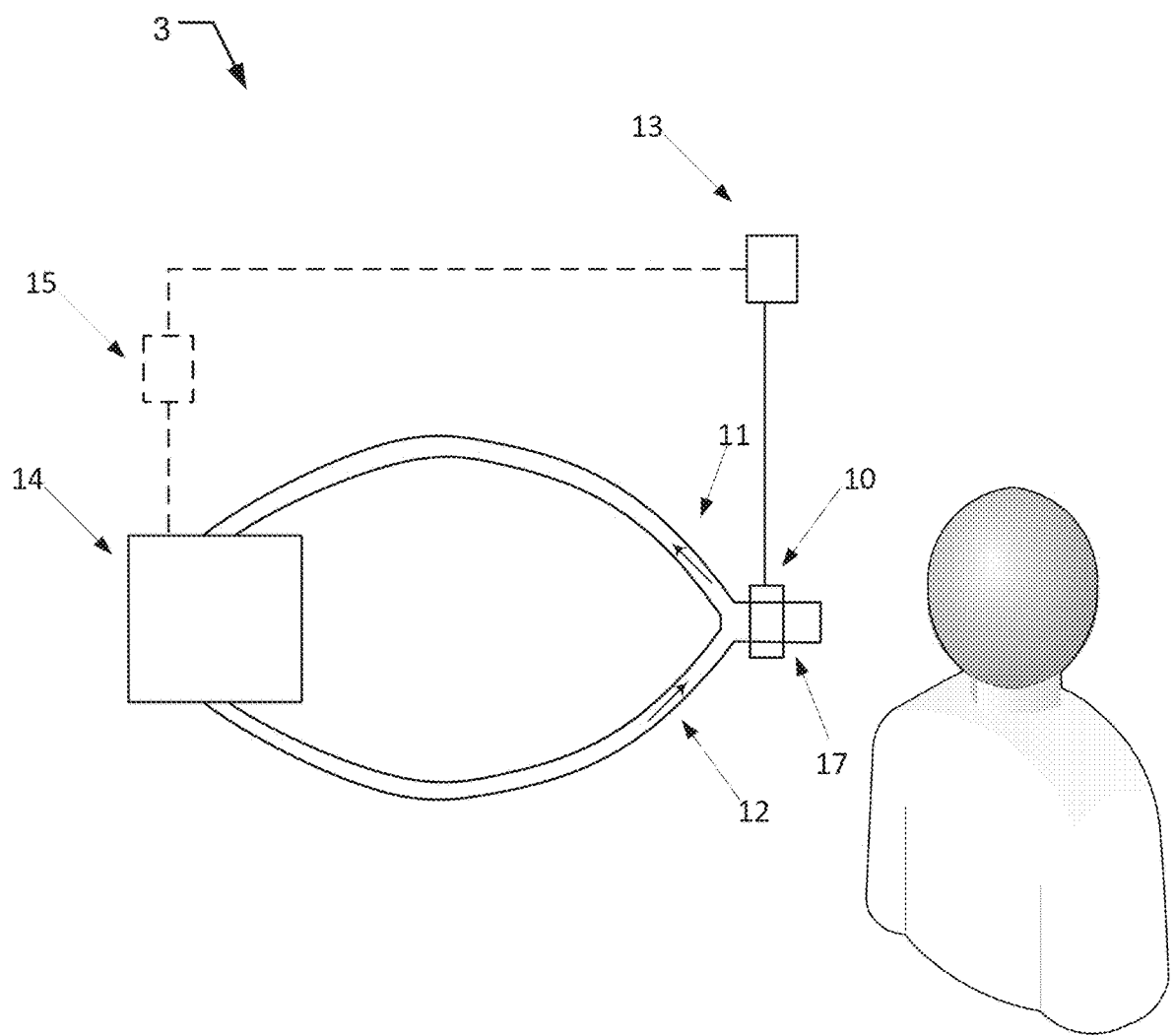

In FIG. 1D a further configuration 3 is illustrated, the particle detection unit is connected before (upstream) the Y-piece, making it possible to measure or detect particles in both expiration and inspiration gases. This may alternatively be made in a side stream configuration as in FIG. 1B.

Figure 1E:
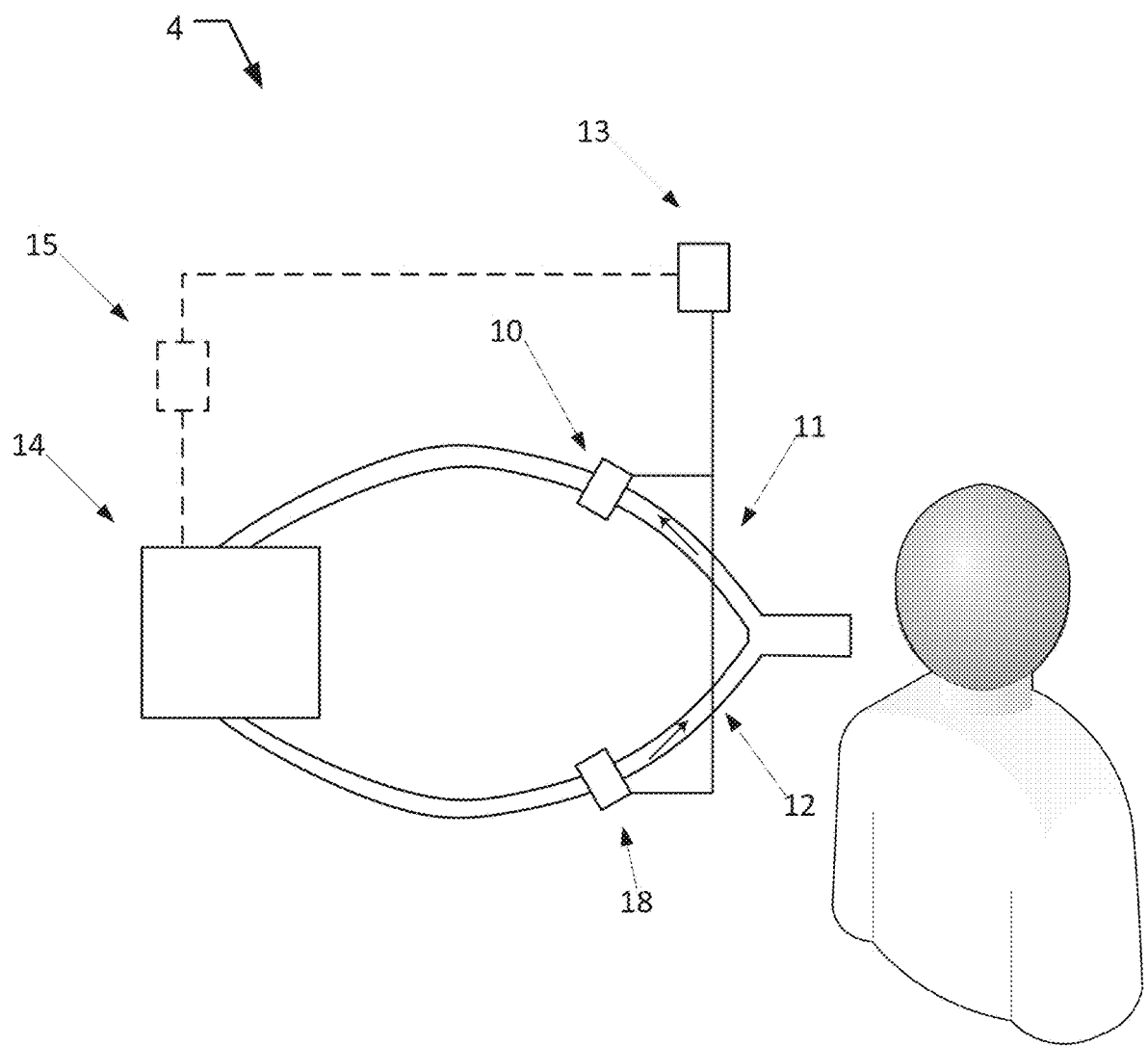

Alternatively as in the configuration 4 depicted in FIG. 1E, one particle detection unit 10 is connected to the expiration conduit 11 and one particle detection unit 18 is connected to the inspiration conduit 12.

By measuring on both the expiration and inspiration gases the particle entering the airways may be characterized and used in the analysis. For example detection of particles in inspiration gases may provide a warning to increase safety since particles in the inspiration gases may indicate failure of, for example, a filter.

Alternatively and/or additionally, detection of particles in the inspiration gases may also provide a warning, such as during delivery of anaesthesia to a patient, that a delivered medicament is not fully evaporated.

Alternatively and/or additionally, detection of an amount of particles in the inspiration gases may also provide a possibility of estimate the amount of medicament delivered. For example, those instances when the medicament is delivered as aerosols in the inspiration conduit.

When continuously monitoring the exhaled air an increase in particles may indicate collapses of a patient's airways, such as lung. Thus a warning may be sent to medical staff from the interface 13.

Alternatively and/or additionally, in some examples, the information related to a detected increase in exhaled particles may also be used to automatically adjust, for example the PEEP to avoid opening and closing and thereby avoid decrease in surfactants that may lead to multi organ failure or death, using the control unit 15 connected to the ventilator 14.

Further, some examples of the disclosure also provide for a warning of acute respiratory distress syndrome (ARDS) or acute lung injury (ALI) for instance due to trauma; or sepsis; or collapse of lung; or acute lung injury. The warning may be provided upon to detection of a rapid increase in particles in the exhaled breath.

Figure 2:
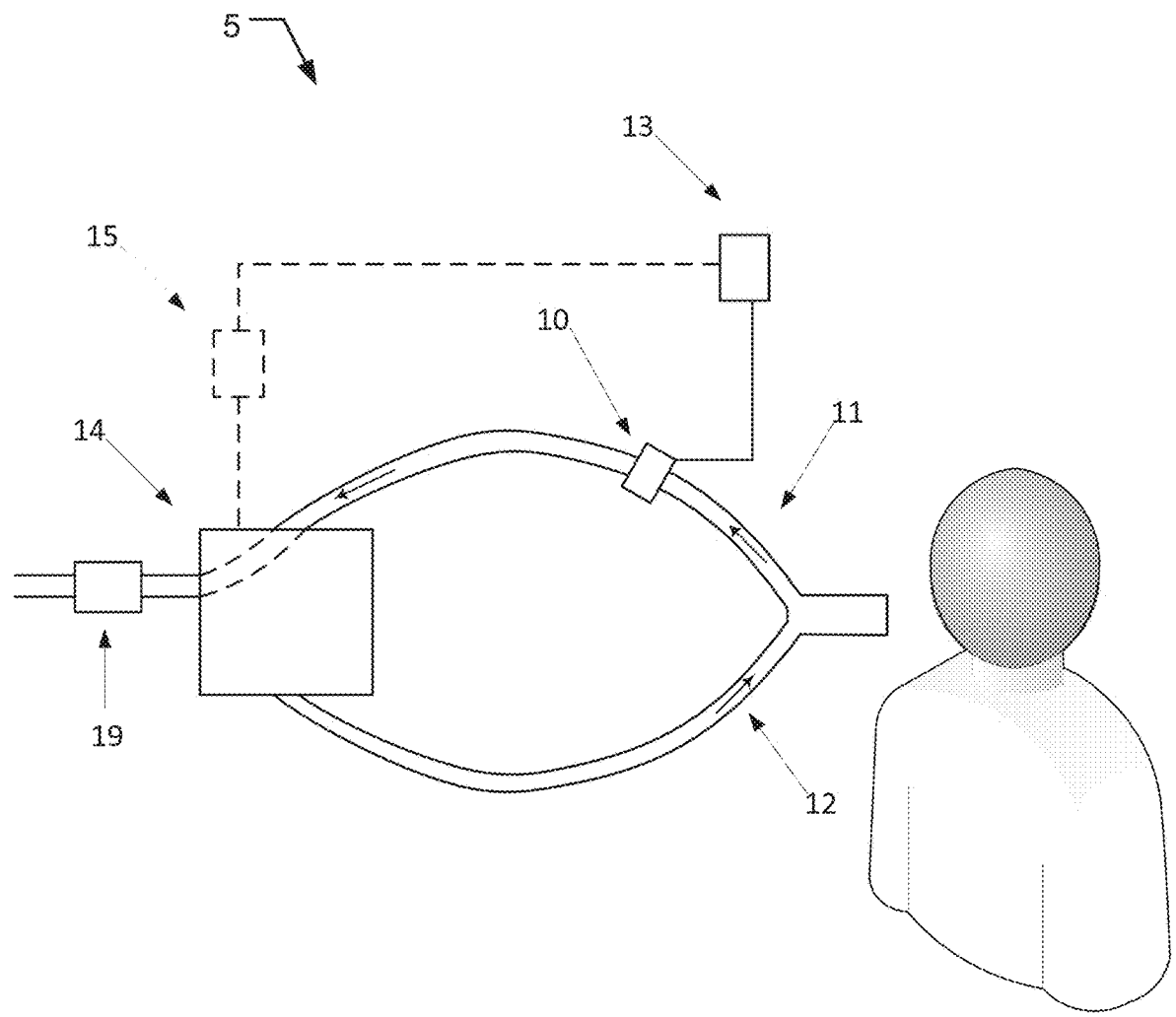
FIG. 2 is showing a schematic illustration of an exemplary system using both a particle detecting unit for continues particle quantification and a collection unit, such as an impactor, according to the disclosure.

In FIG. 2, an embodiment of a system 5 comprising a further particle collection unit 19 is illustrated. This collection unit is used to collect or sample volatile, semi-volatile and/or non-volatile compounds or materials in the exhaled breath. Alternatively and/or additionally, the collection unit 19 may be used to collect or sample particles being vehicles for transporting such compounds or materials, for example non-volatile compounds transported by aerosol particles.

The collection unit 19 may be a cascade impactor, such as a commercially available PM10 Impactor, Dekati Ltd, Tampera, Finland. It should be noted that the PM10 Impactor is only known for other purposes and uses than the herein described.

Alternatively the collection unit may also be a particle trap (adsorptive, cryogenic, chemical), or at least one filter, or a collection chamber, or electrostatic collection components, or sampling bags or canisters, Solid-phase extraction SPE membrane, sorbent tubes, condensation components (such as surface condensation collectors), or utilizing surface functionalization, or any other type of collectors suitable for collecting particles from exhaled fluids.

The particle collection unit 19 is here illustrated to be connectable downstream the ventilator 14. Thus the ventilator may not be affected by a pressure drop, such an impactor may cause on the system. The exhaust gas from the ventilator 14 is flowing through the particle collection unit 19 either driven by a pump (not shown) or by the under pressure provided by an evacuation system (not shown).

Alternatively the particle collection unit 19 may be connected at other locations on the conduit 11 or by utilizing a side stream, but then a compensation for any pressure drops may be needed, for example by using a pump.

The detection unit 10 is here illustrated to be positioned at the exhalation conduit 11 but may in some examples be positioned at any position hereinabove described in conjunction with FIG. 1A to FIG. 1E.

Alternatively the detection unit 10 may be positioned apposition to the collection unit, such as in or after the ventilator 14.

The particle collection unit 19, e.g. a suitable impactor, has an inlet and an outlet, and comprising a plurality of stages arranged such that a gas stream comprising particles enters the impactor via the inlet and passes through each stage in turn before exiting the impactor via said outlet. Each stage of the impactor is separated from adjacent stages by a partition having an orifice which directs the gas stream towards collection plates, the major face of each collection plate being arranged substantially perpendicular to the direction of flow of the gas stream. Exhaled particles are passed through the inertial impactor in a gas stream, such that the primary gas stream is directed towards each collection plates in each stage in turn. The at least first collection plate located in a first stage collects particles of a first mass and at least a second collection plate located in a second stage collects particles of a second mass. In this way a particle profile is obtained. After being sorted according to their size or mass, particles are analyzed.

They may be analyzed by at least one analysis technique selected from the group consisting of: time-of-flight secondary ion mass spectrometry (TOP-SIMS), matrix assisted laser desorption ionization mass spectrometry (MALDI-MS), gas-chromatography mass spectrometry (GCMS), liquid chromatography mass spectrometry (LCMS), or other mass spectrometric techniques, biochemical assays or protocols based on labelled antibodies, such as multiplex Elisa plates, quantitative PCR analysis, scanning electron microscopy (SEM), surface plasmon resonance (SPR), fluorescence spectroscopy, Raman spectroscopy, Surface enhanced Raman spectroscopy (SERS), TOC (total organic content) analysis, elemental analysis and inductively coupled plasma mass spectrometry (ICP-MS), surface acoustic-wave (SAW) and nano-wires for detection of particular proteins with or without being first washed off the collection plates.

The particle collection unit 19 may be used to collect or sample particles or compounds in exhaled breath for chemical, biological DNA, virological and bacteriological analysis of the particles.

These analyses may be carried out off-line. Alternatively, using some of the analysis techniques mentioned above, it may in some examples be preferable to carry out these analyses on-line. A possible implementation of an embodiment for on-line analysis may be use of SERS-technique in combination with the impactor, such as use of specific surface coatings i.e. SERS-substrates, metal-doped sol-gel, derivatizationable coatings or other types of functionalization (i.e. SERS-labeled gene-probes or antibodies).

Diagnosis of ongoing ventilation and adaptation of ventilation strategies may in some examples be made based on both the particles measurements and additionally based on the chemical, biological, DNA/RNA/mRNA, virological and/or bacteriological analysis of the particles themselves.

The analysis conducted using the particle collection unit 19 may provide possibilities of detecting diseases or damages to the airways, such as lungs. The obtain information may be used for diagnosis, monitoring and/or treatment of a patient.

Further, the information provided by the particle collection unit 19 may also in some examples be used to optimize the ventilation of the patient.

The collection time of the collection unit 19 may be similar to the aforementioned times for the particle detection unit 10.

Additionally and/or alternatively, in some further examples, a collector unit, such as an impactor, may be used to quantifying the number of particles by weight. By collecting specific size and/or mass ranges of particles on the collection plates, the number of particles exhaled during a particular collection time may be estimated.

Additionally and/or alternatively, in some examples of a system having a particle collection units 19 connected to the expiration air, the ventilator may be used to control the patient's breathing to optimize the collection of particles. The ventilator may for example be controlled so that the patient is simulated to hold his breath for a period of time before performing a deep exhalation.

Additionally and/or alternatively, the performing measurements it may be advantageous if the particle collection unit is kept at a temperature such that the size distribution of the exhaled aerosol is not changed either by evaporation or condensation of water vapor.

The same may also apply for the measurements using the particle detection unit.

By keeping the temperature substantially stable, the size distribution of the exhaled aerosol is not changed when obtaining a particle distribution profile of the particles.

The exhaled air passes an opening into the particle collection unit which is located in a thermostated compartment, also here with the purpose of maintaining the aerosol size distribution. In some examples of a particle detection unit, in the compartment is located a reservoir for the exhaled air. In these examples, an inertial impactor for the collection of particles is connected to the reservoir first opening.

A sample is taken in the following way by the particle collection unit when being an impactor. It is assumed that the impactor is loaded with clean collection plates, and that the system, especially the impactor, has attained the desired temperature. First, the flow meter is zeroed to allow a proper measurement of flows, and then the moist clean air flow is set at a value so that a positive flow will be maintained from the system during measurement. Then the impactor flow is set at a value lower than the clean air flow. During this procedure, no deposit will be collected on the plates, since the system is fed by clean particle free air. Then the optical particle counter is started and it is checked that no spurious particles are present, e.g. indicating a leak into the system. Exhalation into the system then begins; the particle counter continuously draws a sample and produces a size distribution every six seconds while the impactor collects samples for later analysis. When a required amount of sample has been obtained, the collection is terminated, the time of sampling and exhaled volume recorded. The flow through the impactor is turned off, the impactor removed from the measurement system and the loaded plates are recovered.

Figure 3:
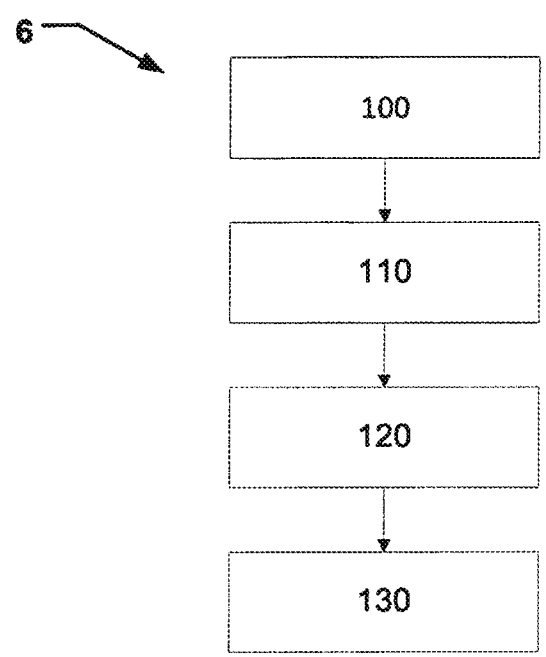
FIG. 3 is schematically illustrating an exemplary embodiment of a method according to the disclosure.

A further aspect of the disclosure provides for a method 6 illustrated schematically in FIG. 3.

The method 6 provides diagnosis and/or monitoring of a condition of a patient connected to a ventilator. The method 6 is carried out by providing 100 a particle detecting unit connected to a conduit for passing expiration fluid from said patient. Further, the method comprises a step of obtaining data 110 related particles exhaled from said patient's airways.

Optionally, in some examples, the related data may be analyzed to provide further information concerning the state of the ventilated patient's airways, for example the amount and/or size and/or mass profile of the detected particles.

The obtained data or information may be used by medical staff to improve the treatment of the ventilated patient, such as optimizing the mechanical ventilator.

Additionally and or alternatively, the information may optionally be used for automatically adjusting 120 the mechanical ventilator using a control unit similar to what has previously been described.

Additionally, a particle collection unit may be provided 130 to obtain further information which may be used in diagnosing and/or monitoring the patient.

The disclosure also relates to use of a particle counter to measure a number of particles in exhaled breath from a patient ventilated by a mechanical ventilator or respirator, for diagnosis or monitoring of the patient's airways.

Additionally and/or alternatively to some examples of the disclosure, the data from the particle counter is used for controlling the mechanical ventilator or respirator, such as controlling PEEP, tidal volume, CPAP etc.

Figure 4A:
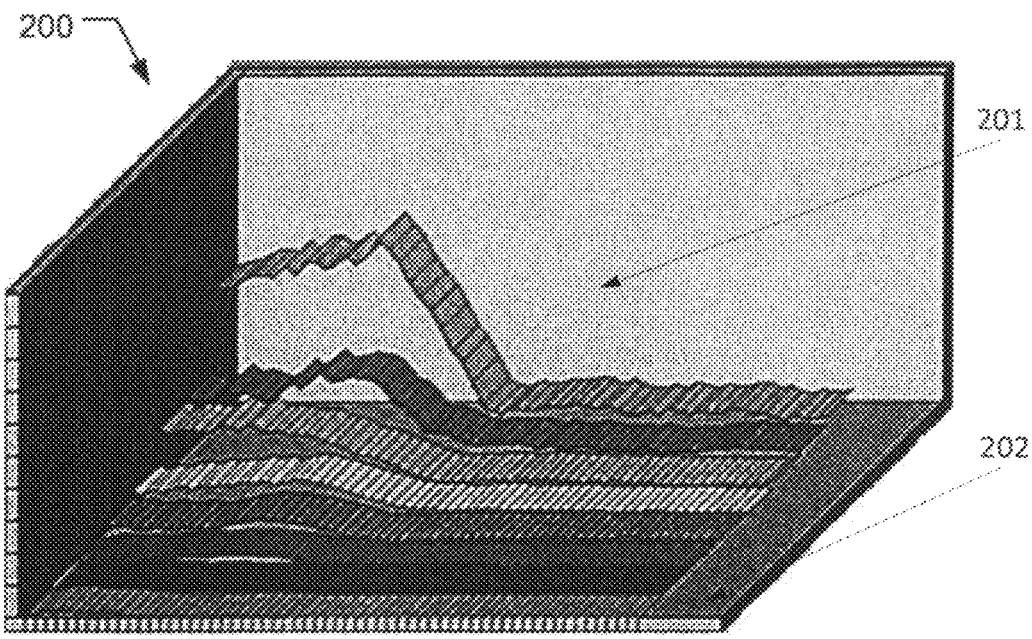
FIG. 4A is showing an decrease in different size fractions after an increase in PEEP.
Figure 4B:
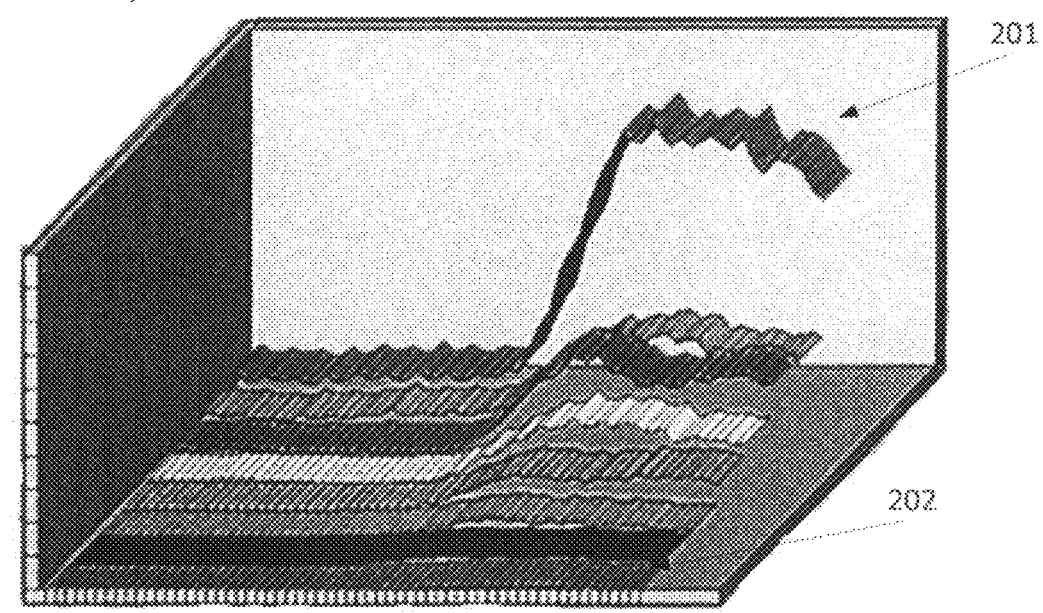
FIG. 4B is showing an increase in different size fractions after a decrease in PEEP.

FIG. 4A and FIG. 4B illustrates clinical observations at patients having Adult respiratory distress syndrome and treated using mechanical ventilation. The graph 200 in FIG. 4A is showing particles in exhaled air when increasing the PEEP. The particles are measured using a particle detection unit. The graphs show a clear decrease in particles in the exhaled air for all size fractions. The curves in the graph 200 illustrate different ranges of particle sizes. The top curve 201 shows particles with a diameter larger than 2 microns and the lowest curve 202 shows particle with a diameter between 0.3 and 0.4 microns. In this exemplary measurement the decrease happened about 10 to 20 seconds after the increase of PEEP. In other examples the decrease may happen earlier or immediately after an increase of PEEP. In some other examples, the decrease may happen later than 20 seconds.

The graph 210 in FIG. 4B is showing particles in exhaled air measured in conjunction with a decrease in PEEP. The graphs show a clear increase in particles in the exhaled air for all size fractions. The curves in the graph 210 illustrate different ranges of particle sizes the top curve 201 in the graph 210 is showing particles with a diameter larger than 2 microns and the lowest curve 202 shows particles with a diameter between 0.3 and 0.4 microns. In this exemplary measurement, the increase happened about 10 to 20 seconds after the decrease of PEEP. In other examples the increase may happen earlier or immediately after a decrease of PEEP. In some other examples, the increase may happen later than 20 seconds.

Studies on healthy patients have shown a correlation between opening of the airways, after a closure, and an increase of particles in the exhaled air. This means that these measurements may be an indication of how well collapsed parts of a lung have been kept open using optimal PEEP during treatment by a mechanical ventilator.

Examples of the present disclosure are described herein with reference to flowchart and/or block diagrams. It will be understood that some or all of the illustrated blocks may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It is to be understood that the functions/acts noted in the diagrams may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims the steps or acts of the method are recited.

The invention claimed is:

1. A diagnostic device for characterization of particles from a patient's airways, when the patient is ventilated by a ventilator, comprising:
   a particle detector configured to be connected to a conduit for passing expiration fluid from said patient, said particle detector being configured for obtaining particle data related to physical properties of particles exhaled from said patient's airways, wherein said particles are aerosols, and wherein said physical properties includes at least number of particles and size; and
   a programmable data processing apparatus configured to analyze said particle data obtained by said particle detector and to detect at least a partial collapse of a lung;
   wherein said programmable data processing apparatus is configured to adjust said ventilator based on said particle data related to physical properties of said particles.

2. The diagnostic device of claim 1, wherein said particle detector is a particle counter or sizer.

3. The diagnostic device of claim 1, wherein said conduit is an expiration conduit downstream a Y-connector connectable to said patient.

4. The diagnostic device of claim 1, wherein said conduit is a side-stream conduit connected to an expiration conduit downstream a Y-connector connectable to said patient.

5. The diagnostic device of claim 1, wherein said particle detector is configured to be connected to both an expiration conduit and an inspiration conduit.

6. The diagnostic device of claim 1, wherein said programmable data processing apparatus is configured to adjust said ventilator to provide a mechanical ventilation mode based on said data related to particles being exhaled from said patient's airways.

7. The diagnostic device of claim 1, wherein said particle detector is an optical based particle counter or sizer.

8. The diagnostic device of claim 1, wherein said programmable data processing apparatus is configured to control a positive end expiratory pressure (PEEP), tidal volumes and/or continuous positive airway pressure (CPAP), based on said particle data related to physical properties of said particles.

9. The diagnostic device of claim 1, further comprising a particle collector configured to be connected to said conduit downstream said ventilator.

10. The diagnostic device of claim 9, wherein the particle collector is an impactor.

11. The diagnostic device of claim 1, further comprising a display unit configured to display information indicating a change in at least one of the number or size of said particles and provide a warning associated with the partially collapsed lung responsive to the change in at least one of the number or size of said particles.

12. A diagnostic device for characterization of particles from a patient's airways when the patient is ventilated by a ventilator, comprising:
a particle detector configured to be connected to a conduit for passing expiration fluid from said patient, said particle detector being configured for obtaining particle data related to physical properties of particles exhaled from said patient's airways;
wherein said particles are aerosols, and wherein said physical properties includes at least number of particles and size; and
a programmable data processing apparatus configured to analyze said particle data obtained by said particle detector to detect at least a partial collapse of a lung and adjust said ventilator based on said particle data related to physical properties of said particles by optimizing positive end expiratory pressure (PEEP) and/or continuous positive airway pressure (CPAP) to mitigate a partial collapse of a lung of said patient's airways and/or avoid over dimension, over distension, and abrasive damages of said lung.

13. The diagnostic device of claim 12, wherein said programmable data processing apparatus is configured for analyzing said particle data obtained only by said particle detector.

14. The diagnostic device of claim 12, further comprising a particle collector configured to be connected to said conduit downstream said ventilator, the particle collector configured to obtain said particle data related to physical properties of particles exhaled from said patient's airways, wherein said particles are collected by collection plates in said particle collector and sorted according to their size or mass.

15. The diagnostic device of claim 12, further comprising a particle collector configured to be connected to said conduit downstream said ventilator, the particle collector configured to obtain said particle data related to physical properties of particles exhaled from said patient's airways, wherein the particle collector is an impactor.

16. The diagnostic device of claim 12, wherein said particle detector is an optical based particle counter or sizer.

* * * * *